US007919121B2

(12) United States Patent
Badylak et al.

(10) Patent No.: US 7,919,121 B2
(45) Date of Patent: Apr. 5, 2011

(54) BIOMATERIAL DERIVED FROM VERTEBRATE LIVER TISSUE

(75) Inventors: Stephen Francis Badylak, West Lafayette, IN (US); Eric James Rodenberg, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 69 days.

(21) Appl. No.: 10/500,511

(22) PCT Filed: Jan. 9, 2003

(86) PCT No.: PCT/US03/00604
§ 371 (c)(1),
(2), (4) Date: Jun. 30, 2004

(87) PCT Pub. No.: WO03/059061
PCT Pub. Date: Jul. 24, 2003

(65) Prior Publication Data
US 2005/0019419 A1    Jan. 27, 2005

Related U.S. Application Data

(60) Provisional application No. 60/347,541, filed on Jan. 11, 2002.

(51) Int. Cl.
*A61K 35/12* (2006.01)
*A61K 35/407* (2006.01)
*A61K 35/32* (2006.01)
*A61K 35/36* (2006.01)

(52) U.S. Cl. ......... 424/574; 424/520; 424/553; 424/572
(58) Field of Classification Search .................. 424/520, 424/550, 553, 572, 574
See application file for complete search history.

(56) References Cited

U.S. PATENT DOCUMENTS

| | | | |
|---|---|---|---|
| 4,352,887 A | 10/1982 | Reid et al. | |
| 4,399,123 A | 8/1983 | Oliver et al. | |
| 4,642,292 A | 2/1987 | Reid et al. | |
| 4,645,669 A | 2/1987 | Reid | |
| 4,801,299 A | 1/1989 | Brendel et al. | |
| 4,829,000 A | 5/1989 | Kleinman et al. | |
| 4,902,508 A | 2/1990 | Badylak et al. | |
| 5,275,826 A | 1/1994 | Badylak et al. | |
| 5,281,422 A | 1/1994 | Badylak et al. | |
| 5,352,463 A | 10/1994 | Badylak et al. | |
| 5,510,254 A | 4/1996 | Naughton et al. | |
| 5,955,110 A | 9/1999 | Patel et al. | |
| 6,206,931 B1 | 3/2001 | Cook et al. | |
| 6,379,710 B1 * | 4/2002 | Badylak | 424/553 |
| 6,734,018 B2 * | 5/2004 | Wolfinbarger et al. | 435/378 |
| 6,793,939 B2 | 9/2004 | Badylak | |
| 6,866,686 B2 * | 3/2005 | Ollerenshaw et al. | 623/23.72 |
| 7,175,841 B2 * | 2/2007 | Badylak et al. | 424/93.7 |
| 7,482,025 B2 | 1/2009 | Badylak | |
| 2002/0160052 A1 | 10/2002 | Badylak | |
| 2003/0216812 A1 | 11/2003 | Badylak | |
| 2004/0157323 A1 | 8/2004 | Badylak | |
| 2004/0187877 A1 | 9/2004 | Badylak et al. | |
| 2004/0191226 A1 | 9/2004 | Badylak | |
| 2009/0123511 A1 | 5/2009 | Badylak | |

FOREIGN PATENT DOCUMENTS

| | | | |
|---|---|---|---|
| EP | 218 065 | | 4/1987 |
| WO | WO 98/25637 | * | 6/1998 |
| WO | 03/084410 | | 10/2003 |

OTHER PUBLICATIONS

Robinson et al., 1980, European Journal of Biochemistry/FEBS, vol. 111, No. 2, pp. 485-490.*
Brendel et al., 1980, Advances in Experimental Medicine and Biology, vol. 131, pp. 89-103.*
Delriviere, Luc et al., "Detailed Modified Technique for Safer Harvesting and Preparation of Liver Graft in the Rat," 1998, MICROSURGERY, 1996, vol. 17, No. 12, pp. 690-696.
Ryerse, Jan S. et al., "A New Technique for the Isolation and Purification of the Basal Lamina from Insect Tissues," TISSUE & CELL, 1985, vol. 17(2), pp. 287-292.
Lim, Franklin; Sun, Anthony M., "Microencapsulated Islets as Bioartifical Endocrine Pancreas," SCIENCE, Nov. 21, 1980, vol. 210, pp. 908-910.
Badylak, et al., "Strength over Time of a Resorbable Bioscaffold for Body Wall Repair in a Dog Model," *J. Surg. Res.*, vol. 99, pp. 282-287 (2001).
Badylak, et al., "Morphologic Study of Small Intestinal Submucosa as a Body Wall Repair Device," *J. Surg. Res.*, vol. 103, pp. 190-202 (2002).
Kleinman, et al., "Formation of a Supramolecular Complex is Involved in the Reconstruction of Basement Membrane Components," *Biochem.*, vol. 22, pp. 4969-4974 (1983).
Kleinman, et al., "Basement Membrane Complexes with Biological Activity," *Biochem.*, vol. 25(2), pp. 312-318 (1986).
Wewer, et al., "Human Laminin Isolated in a Nearly Intact, Biologically Active Form from Placenta by Limited Proteolysis," *J. of Biol. Chem.*, vol. 258(20), pp. 12654-12660 (1983).
Madison, et al., "Increased Rate of Peripheral Nerve Regeneration Using Bioresorbable Nerve Guides and a Laminin-Containing Gel," *Exp. Neurology*, vol. 88, pp. 767-772 (1985).
Kleinman, et al., Isolation and Characterization of Type IV Procollagen, Laminin, and Heparan Sulfate Proteoglycan from the EHS Sarcoma, *Biochem.*, vol. 21, pp. 6188-6193 (1982).
Vukicevic, et al., "Identification of Multiple Active Growth Factors in Basement Membrane Matrigel Suggests Caution in Interpretation of Cellular Activity Related to Extracellular Matrix Components," *Exp. Cell Res.*, vol. 202, pp. 1-8 (1992).
Saad, et al., "Crude Liver Membrane Fractions and Extracellular Matrix Components as Substrata Regulate Differently the Preservation and Inducibility of Cytochrome Patent-450 Isoenzymes in Cultured Rat Hepatocytes," *Eur. J. Biochem.*, vol. 213, pp. 805-814 (1993).

(Continued)

*Primary Examiner* — Shin-Lin Chen
(74) *Attorney, Agent, or Firm* — Barnes & Thornburg LLP

(57) ABSTRACT

A tissue graft composition comprising liver basement membrane and a method of preparation of this tissue graft composition are described. The graft composition can be implanted to replace or induce the repair of damaged or diseased tissues.

8 Claims, No Drawings

OTHER PUBLICATIONS

Saad, et al., "Crude Liver Membrane Fractions as Substrate Preserve Liver-Specific Functions in Long-Term Serum-Free Rat Hepatocyte Cultures in Vitro," *Cell Dev. Biol.*, vol. 29A, p. 3240 (1993).

Rakotoarivony, et al., Comptes Rendus Hebdomadaires des Seances de L'Acedemie des Sciences D: Sciences Natruelles, vol. 284(7), pp. 565-568 (1977) (abstract).

Carlson, et al., *Renal Physiology*, vol. 3(1-6), pp. 280-287 (1980) (abstract).

Meezan, et al., *Biol Chem. Basement Membrane* [*Proc. Intl Symp.*] $1^{st}$, pp. 17-30 (1978) (abstract).

Dixit, et al., *Artificial Organs*, vol. 16(4), pp. 336-341 (1992) (abstract).

Gibbons, et al., *Eur. J. Biochem.*, vol. 66(2), pp. 243-250 (1976) (abstract).

Dunn et al., "Long-Term in Vitro Function of Adult Hepatocytes in a Collagen Sandwich Configuration," *Biotechnology Prog.*, 7: 237-245 (1991).

Bhatia et al., "Microfabrication of Hepatocyte/Fibroblast Co-Cultures: Role of Homotypic Cell Interactions," *Biotechnology Prog.*, 14: 378-387 (1998).

Behnia et al., "Xenobiotic Metabolism by Cultured Primary Porcine Hepatocytes," *Tissue Engineering*, 6: 467-479 (2000).

Yamamoto et al., *Hepatology Research*, 35(3):169-77 (2006) (Abstract only).

Campbell, L.H. et al., *In Vitro Cell Dev. Bio. Meeting Abstract Issue*, 2007 (Abstract A-2000).

Wang, Ying-Jie et al., *World J. Gastroenterol.*, 10(5):699-702 (2004).

Bissell et al., "Support of Cultured Hepatocytes by a Laminin-rich Gel", Journal of Clinical Investigation, (Mar. 1987) vol. 79, pp. 801-812.

\* cited by examiner

BIOMATERIAL DERIVED FROM VERTEBRATE LIVER TISSUE

CROSS-REFERENCE TO RELATED APPLICATIONS

This application is a U.S. national counterpart application of international application serial no. PCT/US03/00604 filed Jan. 9, 2003, which claims the benefit of U.S. provisional application Ser. No. 60/347,541 filed Jan. 11, 2002.

FIELD OF THE INVENTION

The present invention relates to a tissue graft composition and methods for its preparation and use. More particularly, the present invention is directed to a method for preparing a non-immunogenic tissue graft composition comprising the basement membrane of liver. The composition can also be used to promote endogenous tissue growth in vivo and to support the growth and differentiation of cells cultured in vitro.

BACKGROUND AND SUMMARY OF THE INVENTION

There has been much research effort directed to finding natural and synthetic materials having the requisite properties for use as tissue grafts. Surprisingly, it has been found that basement membranes (stroma) prepared from liver tissue of warm-blooded vertebrates by removing cellular components of the liver tissue exhibit certain mechanical and biotropic properties similar to that which has been reported for intestinal submucosal tissue in U.S. Pats. Nos. 4,902,508; 5,281,422; and 5,275,826. Liver basement membranes can be substituted for intestinal submucosa tissue in most, if not all, of the applications previously reported for intestinal submucosa, including enhancing wound healing, promoting endogenous tissue growth, and stimulating cell proliferation and inducing cell differentiation in vivo and in vitro. See U.S. Pat. No. 6,379,710.

The basement membrane of the liver is an extracellular matrix distinct from submucosal extracellular matrices. Liver basement membrane does not support an overlaying mucosa and is devoid of the laminate tissue structure in which submucosal extracellular matrices reside. Liver tissues play a central role in numerous regulatory processes in the body, including glucose metabolism, insulin regulation, anabolic processes for the musculo-skeletal system and central nervous system, and the maintenance of appropriate levels of circulating proteins essential for day to day homeostasis.

U.S. Pat. No. 6,379,710 describes methods for isolating liver basement membranes. However, there has been an ongoing research effort to develop a liver basement membrane preparation/purification protocol that can be used to produce a liver basement membrane preparation in a more pure form (e.g., devoid of cells, cell components, endotoxin, and DNA of liver tissue). The present liver basement membrane preparation can be used to efficiently produce tissue graft materials with more consistent physical properties and more acceptable clinical characteristics.

Accordingly, one embodiment of this invention provides a method for preparing a substantially pure tissue graft composition comprising basement membrane of warm-blooded vertebrate liver tissue. The method comprises the steps of partially hydrolyzing liver tissue by contacting the tissue with an aqueous composition comprising an exogenous protease, washing the liver tissue with an aqueous detergent composition comprising a non-denaturing detergent, removing the non-denaturing detergent, and washing the liver tissue with a composition comprising a denaturing detergent substantially free of non-denaturing detergent. The graft composition so prepared comprises an extracellular matrix consisting essentially of liver basement membrane devoid of endogenous cells associated with the liver tissue. In another embodiment, a liver basement membrane composition prepared according to this method is provided.

The graft composition so prepared is useful for inducing the formation of endogenous tissue at a site in need of endogenous tissue growth in a warm-blooded vertebrate. Thus, another embodiment of this invention is a method comprising the step of implanting into the vertebrate the graft composition prepared as described above comprising basement membrane of liver tissue of a warm-blooded vertebrate in an amount effective to induce endogenous tissue growth at the site of administration of the graft composition.

The liver basement membrane graft composition prepared in accordance with this invention can be used to manufacture a non-immunogenic tissue graft composition for use in the repair of damaged or diseased tissues. The tissue graft composition comprises the basement membrane of liver tissue of a warm-blooded vertebrate substantially free, preferably devoid, of endogenous cells (e.g., hepatocytes and bile duct cells) and cell components of the warm-blooded vertebrate and devoid of endotoxin and DNA. The tissue graft composition can be implanted, or fluidized and injected, into a vertebrate host to contact damaged, defective, or missing tissues and induce the repair or replacement of the tissues. The tissue graft composition can also be applied as a component of a wound dressing (ointment or bandage) in fluidized or solid form for topical application to promote wound healing.

The liver tissue derived graft composition of this invention can also be utilized as a cell growth substrate for growing cells in vitro. Thus, in another embodiment, a liver tissue derived basement membrane composition for supporting the growth of a cell population is provided. The composition comprises the liver basement membrane composition described above, wherein the liver basement membrane is devoid of source liver tissue endogenous cells, and added nutrients to support the growth of the cell population in vitro. In an alternate embodiment, a liver tissue derived basement membrane composition for supporting the growth of a cell population is provided. The composition comprises culture-ware coated with a matrix comprising the liver basement membrane composition prepared as described above wherein the liver basement membrane is devoid of source liver tissue endogenous cells.

DETAILED DESCRIPTION OF THE INVENTION

The tissue graft composition in accordance with the invention comprises liver basement membrane prepared by separating the liver basement membranes from such components of liver tissue of a warm-blooded vertebrate as natively associated cells and cell components, endotoxins, and DNA. The preparative techniques described below provide an extracellular matrix composition consisting essentially of liver basement membrane substantially free of such components. These extracellular matrix compositions are referred to herein generically as liver basement membrane (LBM).

In accordance with this invention "substantially pure tissue graft composition" means a liver basement membrane graft composition substantially free of cells, cell components, and other components such as endotoxin and DNA. The substantially pure liver basement membrane graft composition is prepared according to the procedure described herein.

In accordance with this invention "contacting" liver tissue with a solution in liquid form means suspending the liver tissue in the liquid solution.

Basement membranes for use in the graft composition in accordance with the invention are typically prepared from liver tissue harvested from animals raised for meat production, including, for example, pigs, cattle and sheep or other warm-blooded vertebrates. Thus, there is an inexpensive commercial source of liver tissue for use in preparation of the tissue graft compositions in accordance with the invention. In accordance with one embodiment, a composition comprising liver basement membranes is prepared from liver tissue of a warm-blooded vertebrate. This composition is useful as a non-immunogenic tissue graft capable of inducing endogenous tissue growth when implanted in warm-blooded vertebrates. In one embodiment, the composition comprises an extracellular matrix consisting essentially of liver basement membrane devoid of endogenous cells and other components associated with the source vertebrate liver tissue used to prepare the composition.

The preparation of liver basement membrane from liver tissue of a warm-blooded vertebrate in accordance with the invention is carried out by removing cells, cellular components, and other components, such as endotoxin and DNA, from liver tissue. Ideally the process is carried out to separate the cells, cell components, and other components such as endotoxin and DNA, from the basement membranes without damaging, or at least minimizing disruption or damage to, the basement membrane tissue. Removal of these components from the liver extracellular matrix results in the preparation of a graft composition that is non-immunogenic, and, thus, does not induce an adverse host immune response when the graft composition is implanted into a host.

In general, the method for preparing a basement membrane tissue graft composition from warm-blooded vertebrate liver tissue comprises the steps of protease digestion and treating the liver tissue with a non-denaturing detergent followed by treatment with a denaturing detergent for a period of time sufficient to release cells, cellular components, and other components, such as endotoxin and DNA, from the extracellular matrix without substantial disruption of the extracellular matrix, and separating the dissociated components from the extracellular matrix. Typically the liver tissue is sliced into sheets or strips having a thickness of up to about 2000µ before subjecting the liver tissue to protease digestion.

The first step in preparing LBM in accordance with one embodiment comprises slicing a segment of fresh or frozen liver tissue into pieces (e.g., strips or sheets) to increase the surface area-to-volume ratio of the liver tissue. In one embodiment, the liver tissue is sliced into a series of sheets each having a thickness of about 50 to about 2000 microns, preferably about 100 to about 1000 microns, more preferably about 200 to about 600 microns. Freshly harvested liver tissue can be sliced using a standard meat slicer, or the tissue can be frozen and sliced with a meat slicer or cryomicrotone. In one embodiment, prior to slicing, the liver can be separated into lobes, trimmed, cut into uniform rectangular pieces, and can be frozen.

Before contacting the liver tissue with the protease-containing solution for a time sufficient to release cells, cellular components such as DNA, and endotoxin from the matrix, the liver sheets or strips can be rinsed one or more times, such as with deionized water, saline, or a buffered solution and optionally stored in a frozen hydrated state or a partially dehydrated state until used as described above. For example, the liver sheets or strips could be rinsed three times for 30 minutes each with deionized water, saline, or a buffer. Alternatively, the liver slices can be treated with the protease-containing solution without prior rinsing.

The deionized water, saline, or buffer can then be strained from the liver slices, for example, using a sieve, and hepatocytes and hepatocyte cell fragments can be mechanically dissociated from the liver basement membrane. For example, the liver slices can be massaged on a screen or ultrasound can be used to dissociate cells and cell components from the liver basement membrane. This step also hastens lysis of hepatocytes, and if this step is performed, it is done carefully so that the liver slices are not torn.

The thin slices of liver tissue are then contacted with an aqueous composition containing a protease to partially hydrolyze the liver tissue and release liver cells and other components from the extracellular basement membrane matrix. In accordance with one embodiment, the liver tissue is contacted with an aqueous composition comprising an enzyme, for example, a protease, such as trypsin. Other proteases suitable for use in accordance with the invention include pepsin, bromelain, papain, chymotrypsin, lysosomal proteases, cathepsin, alcalase, savinase, chymopapain, clostripain, endoproteinase Asp N, protease V8, proteinase K, subtilisin proteases, thermolysin, plasmin, and pronase. Combinations of proteases can also be used. Because of the collagenous structure of the liver basement membrane and the desire to minimize degradation of the membrane structure during cell dissociation, collagen specific enzyme activity should be minimized in the enzyme compositions used in the protease digestion step.

The liver tissue is typically also contacted with a calcium chelating agent, such as EDTA, concurrently with the protease treatment. Thus, in one embodiment liver tissue is treated by suspending slices or strips of the tissue in a solution containing a protease and EDTA. As an alternative to a protease, the liver tissue can be contacted with any other enzyme that promotes cell dissociation without degrading the basement membrane structure, such as a GAGase, or the liver tissue can be treated with a combination of enzymes. In another embodiment, the liver tissue can be perfused with a protease solution with or without a $Ca^{++}$ chelating agent prior to slicing and after slicing.

In one preferred embodiment the protease digestion step is carried out by contacting liver tissue slices with a solution, optionally with agitation, containing about 0.005% of the protease (e.g., trypsin) by weight to about 2% of the protease by weight, more typically about 0.01% of the protease by weight to about 1% of the protease by weight and containing a calcium chelating agent, such as EDTA, in an amount effective to optimize release and separation of cells and other components from the basement membrane without substantial degradation of the membrane matrix. The concentration of the calcium-chelating agent (e.g., EDTA) is typically about 0.01% of the calcium chelating agent by weight to about 2% of the calcium chelating agent by weight, preferably about 0.02% of the calcium chelating agent by weight to about 1% of the calcium chelating agent by weight. The protease digestion step is preferably carried out with heating, typically at about 37° C. The rinsing and mechanical dissociation steps described above can be repeated after the protease digestion step. Alternatively, mechanical dissociation, for example with ultrasound, can be performed during and/or after the protease digestion step.

The liver slices are then contacted with a solution containing a non-denaturing detergent. This step is preferably carried out at room temperature, and optionally with agitation. The non-denaturing detergent is preferably Triton X-100, typically a Triton X-100 solution of about 0.5% to about 5%, more typically about 2% to about 4%. However, any non-denaturing detergent known in the art which is effective to release cells and other components from the liver basement membrane without substantial disruption of the basement membrane matrix can be used.

Exemplary of non-denaturing detergents that can be used in accordance with the invention are polyoxyethylene ethers, 3-[(3-cholamidopropyl dimethylammonio]-1-propane-sulfonate (CHAPS), nonylphenoxy polyethoxy ethanol, polyoxyethylenesorbitans, sodium lauryl sarcosinate, and alkyl glucosides including $C_8$-$C_9$ alkyl glucoside. Various types of nonylphenoxy polyethoxy ethanol detergents are available including NP-4, NP-7, NP-9, NP-10, NP-35, and NP-40, sold under the trademark Niaproof® (Niacet Corp.), and any of these types, or any other suitable types of this surfactant, can be used in accordance with the invention. Polyoxyethylene ethers include Triton X-100, Triton X-114, Triton X-405, Triton N-101, Triton N-42, Triton N-57, Triton N-60, Triton X-15, Triton X-35, Triton X-45, Triton X-102, Triton X-155, Triton X-165, Triton-X-207, Triton X-305, Triton X-705-70, and Triton B-1956, Triton CG-110, Triton XL-80N, and Triton WR-1339. Any of these polyoxyethylene ethers or other suitable forms can be used. Polyoxyethylenesorbitans that can be used in accordance with the invention include Tween 20, Tween 21, Tween 40, Tween 60, Tween 61, Tween 65, Tween 80, Tween 81, Tween 85, and Span 20.

The rinsing steps described above are repeated after contacting the liver slices with the non-denaturing detergent to remove most, if not all, of the non-denaturing detergent. This step prevents the non-denaturing detergent from interfering with the activity of the denaturing detergent in the subsequent detergent extraction step. The mechanical dissociation steps can be repeated as needed.

After treatment with the non-denaturing detergent, the liver slices are contacted with a solution containing a denaturing detergent. This step is preferably carried out at room temperature and optionally with agitation. The denaturing detergent is preferably deoxycholate, typically a deoxycholate solution of about 0.5% to about 8%, more typically about 2% to about 5%. However, any denaturing detergent known in the art which is effective to release cells and other components from the liver basement membrane without substantial disruption of the basement membrane matrix can be used including such denaturing detergents as sodium dodecylsulfate. The purified LBM is then thoroughly rinsed as described above to remove as much residual detergent as possible and the LBM can be stored (e.g., in deionized water at 4° C.) until further use or can be used immediately following the purification procedure.

The protease digestion step and the treatments with the non-denaturing and denaturing detergents can be performed one or more times to release substantially all of the cells and other components described above from the basement membrane. Additionally, the rinsing steps can be performed one time or multiple times and the mechanical dissociation steps can be repeated as needed or may not be performed if visual inspection indicates that a step to promote mechanical dissociation of cells or other cell components is not required. Moreover, the concentration of the protease and the concentrations of the non-denaturing and denaturing detergents can be varied depending on the thickness of the liver slices used and the specific protease and detergents used in the purification protocol.

Liver basement membrane in accordance with one embodiment can be fluidized (converted to an injectable or powder form) in a manner similar to the preparation of fluidized intestinal submucosa, as described in U.S. Pat. No. 5,275,826 the disclosure of which is expressly incorporated herein by reference. Liver basement membrane (devoid of cells and cell components from the source liver tissue and devoid of endotoxins and DNA) is comminuted by tearing, cutting, grinding, shearing and the like. Grinding the liver basement membrane in a frozen or freeze-dried state is preferred although good results can be obtained as well by subjecting a suspension of liver basement membrane to treatment at a high speed (high shear) in a blender and dewatering, if necessary, by centrifuging and decanting excess water. Additionally, the comminuted fluidized tissue can be solubilized by enzymatic digestion with a protease, for example a collagenase and or other appropriate enzymes, such as glycanase, or other enzymes that disrupt the matrix structural components, for a period of time sufficient to solubilize the tissue and form a substantially homogeneous solution.

The present invention also contemplates the use of powder forms of liver basement membrane. In one embodiment a powder form of liver basement membrane is prepared by pulverizing liver basement membrane under liquid nitrogen to produce particles ranging in size from 0.1 to 1 $mm^2$. The particulate composition is then lyophilized overnight and sterilized to form a solid substantially anhydrous particulate composite. Alternatively, a powder form of liver basement membrane can be formed from fluidized liver basement membranes by drying the suspensions or solutions of comminuted liver basement membrane. The dehydrated forms have been rehydrated and used as cell culture substrates as described below without any apparent loss of their ability to support cell growth.

LBM can also be extracted with guanidine hydrochloride and/or urea, as described in Example 5. Briefly, the powder form of LBM can be suspended in an extraction mixture containing 4M guanidine hydrochloride, 2M urea, and protease inhibitors and may be stirred vigorously. The extraction mixture can then be centrifuged and the supernatant removed and dialyzed extensively to further remove insoluble material. The supernatant can be used immediately or lyophilized and stored for later use.

The present liver basement membrane compositions can be sterilized using conventional sterilization techniques including tanning with glutaraldehyde, formaldehyde tanning at acidic pH, ethylene oxide treatment, propylene oxide treatment, gas plasma sterilization, gamma radiation, and peracetic acid sterilization. A sterilization technique which does not significantly weaken the mechanical strength and biotropic properties of the material is preferably used. For instance, it is believed that strong gamma radiation may cause loss of strength in the graft material. Preferred sterilization techniques include exposing the graft to peracetic acid, low dose gamma irradiation and gas plasma sterilization; peracetic acid sterilization being the most preferred method. In particular, LBM has been disinfected and sterilized through the use of either peracetic acid or one megarad of gamma irradiation without adversely affecting the mechanical properties or biological properties of the tissue. The treatment with peracetic acid is conducted at a pH of about 2 to about 5 in an aqueous ethanolic solution (2-10% ethanol by volume) at a peracid concentration of about 0.03 to about 0.5% by volume. Typically, after the graft composition has been sterilized, the composition is wrapped in a porous plastic wrap and sterilized again using electron beam or gamma irradiation sterilization techniques. A sterilization technique such as that described in U.S. Pat. No. 6,206,931, incorporated herein by reference, may also be used.

In accordance with one embodiment, liver basement membrane is used as, or used to prepare, tissue graft compositions. Such tissue graft compositions lend themselves to a wide variety of surgical applications relating to the repair or replacement of damaged tissues, including, for example the repair of connective tissues. Connective tissues for the purposes of the present invention includes bone, cartilage, muscle, tendons, ligaments, and fibrous tissue including the dermal layer of skin.

In accordance with this embodiment, the tissue graft compositions are used advantageously to induce the formation of endogenous tissue at a desired site in a warm-blooded vertebrate. Compositions comprising an extracellular matrix, consisting essentially of liver basement membrane, can be administered to a vertebrate host in an amount effective to induce endogenous tissue growth at a site in the host in need of repair due to the presence of damaged or diseased tissue. The present liver tissue derived tissue graft compositions can be administered to the host in either solid form, by surgical implantation, or in fluidized form, by injection.

The liver basement membrane can be used in accordance with this invention as a tissue graft construct for use in the repair or replacement of connective tissues using the same procedures described for use of intestinal submucosa in U.S. Pat. Nos. 5,281,422 and 5,352,463, each expressly incorporated herein by reference.

The tissue graft compositions formed and used in accordance with this invention, upon implantation, can undergo biological remodeling. They can serve as a rapidly vascularized matrix for supporting the growth of new endogenous connective tissue. When used as a tissue graft material liver basement membrane is expected to be trophic for host tissues with which it is attached or otherwise associated in its implanted environment.

The liver basement membrane graft composition can be formed in a variety of shapes and configurations, for example, to serve as a ligament or tendon replacement or a patch for a disrupted tendon or ligament. Preferably, the segment is shaped and formed to have a layered or even a multilayered configuration with at least the opposite end portions and/or opposite lateral portions being formed to have multiple layers of the graft material to provide reinforcement for attachment to physiological structures, including bone, tendon, ligament, cartilage and muscle. In a ligament replacement application, opposite ends are attached using standard surgical technique to first and second bones, the bones typically being articulated as in the case of a knee joint, or to remnants of remaining native ligaments.

The end portions of the liver basement membrane graft composition can be formed, manipulated or shaped to be attached, for example, to a bone structure in a manner that will reduce the possibility of graft tearing at the point of attachment. Preferably the material can be folded to provide multiple layers for gripping, for example, with spiked washers or staples or sutured to the bone, for example, to bone tunnels.

Alternatively, the liver basement membrane graft material can be folded back on itself to join the end portions to provide a first connective portion to be attached, for example, to a first bone and a bend in the intermediate portion to provide a second connective portion to be attached to a second bone articulated with respect to the first bone. For example, one of the end portions can be adapted to be pulled through a tunnel in, for example, the femur and attached thereto, while the other of the end portions can be adapted to be pulled through a tunnel in the tibia and attached thereto to provide a substitute for the natural cruciate ligament, the segment being adapted to be placed under tension between the tunnels to provide a ligament function, (i.e., a tensioning and positioning function provided by a normal ligament).

During preparation of the liver basement membrane, the tissue is cut or sliced into sheets/slices. After the processing steps the individual segments of liver basement membrane can be overlapped with one another and bonded together using standard techniques known to those skilled in the art, including the use of sutures, crosslinking agents, and adhesives or pastes. Alternatively, in one embodiment, the overlapped layers of liver basement membrane can be fused to one another by applying pressure to the overlapped regions under dehydrating conditions. The term "dehydrating conditions" is defined to include any mechanical or environmental condition which promotes or induces the removal of water from the liver basement membrane. To promote dehydration of the compressed liver basement membrane tissue, at least one of the two surfaces compressing the tissue is water permeable. Dehydration of the tissue can optionally be further enhanced by applying blotting material, heating the tissue or blowing air across the exterior of the compressing surfaces. Accordingly, multilayer liver basement membrane constructs can be prepared to provide tissue graft compositions of enhanced strength.

In addition, by overlapping a portion of one piece of liver basement membrane with a portion of at least one additional piece of liver basement membrane and bonding the overlapped layers to one another, large area sheets of liver basement membrane can be formed. In one embodiment, during formation of the large area sheets of tissue, pressure is applied to the overlapped portions under dehydrating conditions by compressing the overlapped tissue segments between two surfaces. The two surfaces can be formed from a variety of materials and in any shape depending on the desired form and specification of the targeted graft construct. Typically the two surfaces are formed as flat plates but they can also include other shapes such as screens, opposed cylinders or rollers and complementary nonplanar surfaces. Each of these surfaces can optionally be heated or perforated. In preferred embodiments at least one of the two surfaces is water permeable. The term water permeable surface as used herein includes surfaces that are water absorbent, microporous or macroporous. Macroporous materials include perforated plates or meshes made of plastic, metal, ceramics or wood.

The liver basement membrane can be compressed in accordance with one embodiment by placing the overlapped portions of the strips of cell-dissociated liver membrane on a first surface and placing a second surface on top of the exposed membrane surface. A force is then applied to bias the two surfaces towards one another, compressing the membrane composition between the two surfaces. The biasing force can be generated by any number of methods known to those skilled in the art including the passage of the apparatus through a pair of pinch rollers (the distance between the surface of the two rollers being less than the original distance between the two plates); the application of a weight on the top plate, and the use of a hydraulic press or the application of atmospheric pressure on the two surfaces.

In one preferred embodiment, a multi-layered liver basement membrane graft material is prepared without the use of adhesives or chemical pretreatments by compressing at least the overlapped portions of submucosal tissue under conditions that allow dehydration of the material concurrent with the compression of the tissue. To promote dehydration of the compressed material, at least one of the two surfaces compressing the tissue is water permeable. Dehydration can optionally be further enhanced by applying blotting material, heating the material or blowing air across the exterior of the two compressing surfaces. The compressed multi-layered liver basement membrane material can be removed from the two surfaces as a unitary compliant large area graft construct. The construct can be further manipulated (i.e., cut, folded, sutured, etc.) to suit various medical applications where the liver basement membrane material is required.

A vacuum can optionally be applied to liver basement membrane during the compression procedure ("vacuum pressuring"). The applied vacuum enhances the dehydration of the tissue and may assist the compression of the tissue. Alternatively the application of a vacuum may provide the sole compressing force for compressing the overlapped portions of the multiple layers of liver basement membranes. For example, in one embodiment the overlapped liver basement membrane is laid out between two surfaces, preferably one of which is water permeable. The apparatus is covered with blotting material, to soak up water, and a breather blanket to allow air flow. The apparatus is then placed in a vacuum chamber and a vacuum is applied, generally ranging from 35.6-177.8 cm of Hg (0.49-2.46 Kg/cm$^2$) and more preferably the vacuum applied is approximately 129.5 cm of Hg (1.76 Kg/cm$^2$). Optionally a heating blanket can be placed on top of the chamber to heat the liver basement membrane during compression. Chambers suitable for use in this embodiment are known to those skilled in the art and include any device that is equipped with a vacuum port. The resulting drop in atmospheric pressure coacts with the two surfaces to compress the tissue and simultaneously dehydrate the compressed tissue.

In an alternative embodiment, liver basement membrane can be utilized in a method and composition for supporting the proliferation and induction of tissue differentiation of cells cultured in vitro. Generally the method comprises the step of contacting cells, in vitro, with a liver basement membrane composition under conditions conducive to cell growth. The term "contacting" as used herein with reference to cell culture is intended to include both direct and indirect contact, for example in fluid communication, of the liver basement membrane composition and the cultured cells. The term "conditions conducive to cell growth" as used herein refers to the environmental conditions, such as sterile technique, temperature and nutrient supply, that are considered optimal for cell growth under currently available cell culture procedures. Although optimum cell culture conditions used for culturing cells depend somewhat on the particular cell type, cell growth conditions are generally well known in the art. However, a number of differentiated eukaryotic cell types are still considered difficult to culture (i.e., islets of Langerhans, hepatocytes, chondrocytes, myocardial cells, etc.).

Applicants have discovered that compositions comprising liver basement membrane prepared in accordance with one embodiment of this invention can be used for supporting growth or proliferation of cells in vitro. In accordance with one embodiment a liver tissue derived composition for supporting the growth of a cell population is prepared from liver tissue of a warm-blooded vertebrate. The composition comprises isolated liver basement membrane devoid of source liver tissue endogenous cells and added nutrients to support the growth of said cell population in vitro. In addition, fluidized forms of liver basement membrane can be used to coat culture-ware with a matrix comprising liver basement membrane devoid of source liver tissue endogenous cells. Thus, liver basement membrane can be used as a cell growth substrate in a variety of forms, including a sheet-like configuration, as a gel matrix, as an additive for art-recognized cell/tissue culture media, or as coating for culture-ware to provide a more physiologically relevant substrate that supports and enhances the proliferation of cells.

The liver basement membrane, due to its honeycomb-like structure (that which remains after cell-dissociation) provides a high surface area for cell adhesion and also induces cell differentiation. The membrane material is preferably sterilized prior to use in cell culture applications, however nonsterile material can be used if antibiotics are included in the cell culture system.

In one preferred embodiment cells are seeded directly onto sheets as liver basement membrane under conditions conducive to cell proliferation. The highly porous nature of the liver basement membrane allows diffusion of cell nutrients throughout the membrane matrix. Thus, cells can be cultured on or within the liver basement membrane matrix.

In another embodiment, cell growth substrates are formed from fluidized forms of liver basement membrane. The fluidized tissue can be gelled to form a solid or semi-solid matrix. The viscosity of fluidized tissue for use in accordance with this invention can be manipulated by controlling the concentration of the tissue component and the degree of hydration. The viscosity can be adjusted to a range of about 2 to about 300,000 cps at 25° C. Higher viscosity formulations, for example, gels, can be prepared from the digest solutions by adjusting the pH of such solutions to about 5.0 to about 9.0. Eukaryotic or prokaryotic cells can then be seeded directly on the surface of the gel matrix and cultured under conditions conducive to cell proliferation.

The cell growth substrates of the present invention can be combined with nutrients, including minerals, amino acids, sugars, peptides, proteins, or glycoproteins that facilitate cellular proliferation, such as laminin and fibronectin and growth factors such as epidermal growth factor, platelet-derived growth factor, transforming growth factor beta, or fibroblast growth factor. In one embodiment, fluidized or powder forms of liver basement membrane can be used to supplement standard culture media to enhance the capacity of the standard media for sustaining and inducing the proliferation of cells cultured in vitro.

In accordance with the present invention there is provided a cell culture composition for supporting growth in vitro of a cell population in combination with liver basement membrane of a warm-blooded vertebrate. The composition comprises liver basement membrane substantially free of the originally associated endogenous cells and other components. The composition can further comprise nutrients, and growth factors required for optimal growth of the cultured cells. The liver basement membrane cell culture substrate can be used with commercially available cell culture liquid media (both serum based and serum free). Proliferating cells can either be in direct contact with the liver basement membrane or they can simply be in fluid communication with the liver-basement membrane.

It is anticipated that cell growth compositions utilizing the liver basement membrane composition of the present invention can be used to stimulate proliferation and differentiation of pluripotent stem cells as well as differentiated cells such as islets of Langerhans, hepatocytes and chondrocytes. Furthermore, the described cell growth composition is believed to support the growth of differentiated cells while maintaining the differentiated state of such cells.

It is anticipated that liver basement membrane is capable of inducing host tissue proliferation, remodeling and regeneration of appropriate tissue structures upon implantation in a number of microenvironments in vivo (e.g., tendon, ligament, bone, articular cartilage, artery, and vein). In one embodiment the tissue replacement capabilities of graft compositions comprising liver basement membrane of warm-blooded vertebrates are further enhanced or expanded by seeding the tissue with various cell types, prior to implantation. For example, a liver basement membrane derived cell culture substrate may be seeded with endothelial cells or keratinocytes for use as a vascular graft or skin replacement, respectively. Alternatively, the liver basement membrane can be seeded with mesenchymal cells (stem cells) initially for expansion of the cell population and thereafter for implantation into a host. Liver basement membrane can also serve as a delivery vehicle, either in fluidized form or in its native solid form, for introducing various cell populations, including genetically modified cells, to a specific location in a host. Optionally, after the liver basement membranes have been seeded with eukaryotic cells, the graft composition can be subjected to conditions conducive to the proliferation of cells to further expand the population of the seeded cells prior to implantation of the graft into the host.

In another embodiment, compositions comprising liver basement membrane and a proliferating cell population can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (Science, Vol. 210, pp. 908-910). Indeed, the present liver basement membrane composition itself could be used advantageously to encapsulate a proliferating cell population in accordance with this invention for implantation as an artificial organ.

EXAMPLE 1

Liver Basement Membrane Preparation

Porcine livers were collected and were transported on ice. For each liver, the four lobes were separated using a scalpel/scissors/razor blade and each lobe was trimmed to a fairly uniform rectangular shape. If the liver was to be frozen prior to further processing, each lobe was trimmed and wrapped in a plastic bag and stored in the freezer.

Previously prepared (fresh or frozen) liver lobes were cut using a meat slicer. For cutting, the meat slicer was set to a setting of 1.0 (results in a slice thickness of about 50 microns) and the initial outer layers of the liver membrane were removed by cutting and discarded. Once the outer layers were removed, the meat slicer was set to a setting of 3.0 (results in a slice thickness of about 2000 microns) and the liver slices were cut into slices of uniform thickness. The liver slices were maintained at 4° C. during the cutting process and were stored in the freezer until needed or were used immediately.

Prior to purification (i.e., decellularization), the slices of liver were trimmed with a scalpel/razor blade to remove any remnants on the outer edge of the liver slices from the slicing process. If thickness readings were taken, digital calipers were used and the slices were measured while still frozen. To measure the thickness of the liver slices, the thickness of two small pieces of acrylic was measured using the calipers and the thickness was recorded. A frozen slice of liver was then placed between the acrylic pieces and the combined thickness was measured. The measurements were taken in several areas to get an average liver-acrylic combined thickness. The original thickness of the acrylic pieces was subtracted from the average combined liver-acrylic thickness to obtain the thickness of the liver slices. Generally, the liver slices ranged from about 50 μ to about 2000 μ in thickness.

Solutions for liver basement membrane purification were prepared as follows:

1. 3% (v/v) Triton X-100—For a 500 ml rinse, 15 ml of the concentrated Triton X-100 was added to 485 ml of deionized water. The Triton X-100 is viscous, so it was necessary to do a repeated backwashing of the graduated cylinder to remove residual Triton X-100. The Triton X-100 solution was mixed on a shaker to thoroughly dissolve the detergent in water.

2. 4% (w/v) Deoxycholic Acid—For a 500 ml rinse, 20 g of deoxycholic acid was added to 480 ml of deionized water and the solution was mixed until thoroughly dissolved.

3. 0.02% Trypsin/0.05% EDTA—Trypsin is commonly packaged at a concentration of 25 g/L. Therefore, for a 0.02% solution of trypsin in 500 ml, 0.1 grams of trypsin is required (equivalent to 4 ml of the concentrated trypsin/EDTA solution per 500 ml of deionized water). EDTA (0.05%) is obtained by adding 0.25 g of EDTA (4 ml of trypsin/EDTA solution) to 495.75 ml of deionized water. The solution was agitated on a shaker to ensure adequate mixing.

In general, four liver slices were added per 1500 ml water bottle for each rinsing step, and 500 ml of rinse per 1500 ml water bottle was used. For the first wash, four trimmed liver slices were placed into a 1500 ml water bottle, and 1000 ml of deionized water was added to the water bottle(s). The bottle(s) were placed on a shaker for 30 minutes. After 30 minutes, the water was replaced with fresh deionized water and this process was repeated 2 times, for a total of three 30-minute rinses.

The deionized water was then strained from the liver slices using a sieve, and each liver slice was placed on a standard 12 inch by 12 inch aluminum window screen. Each liver slice was gently massaged by hand or using a rubber rolling pin to hasten the lysis of hepatocytes and to mechanically dissociate hepatocytes from the liver basement membrane. Care was taken to ensure that tears were not created in the slices. At this stage, all of the hepatocytes were not removed from the underlying liver basement membrane. The massaging step was repeated for each liver slice.

The liver slices were then returned in groups of four to the water bottles, and 500 ml of the 0.02% trypsin/0.05% EDTA solution was added to the water bottles. The liver slices were incubated in a 37° C. water bath for 1 hour. After one hour, the trypsin/EDTA solution was strained off using a sieve. Each slice was then momentarily rinsed under a stream of deionized water, and then the massaging step was repeated for each liver slice.

The liver slices were placed back into the bottles and 500 ml of the 3% Triton X-100 solution was added to the bottles. The bottles were placed on a shaker for 1 hour and were then briefly rinsed to remove the detergent solution. If necessary (as determined by visual inspection), the slices were massaged again.

The liver slices were then placed back into the bottles with 500 ml of 4% deoxycholic acid solution. The bottles were placed on the shaker for 1 hour. The purified liver basement membrane was thoroughly rinsed under deionized water for 3 to 5 minutes to remove as much residual detergent as possible. The purified liver basement membrane was stored in sterile deionized water at 4° C. until further use.

EXAMPLE 2

Preparation of Fluidized Liver Basement Membrane

For fluidized or gel forms, the LBM tissue was stored in liquid nitrogen at −80° C. Frozen tissue was then sliced into 1 cm cubes, pulverized under liquid nitrogen with an industrial blender to particles less than 2 mm² and stored at −80° C. prior to use.

Partial digestion of the pulverized material was performed by adding 5 g of the pulverized material to a 100 ml solution containing 0.1% pepsin in 0.5 M acetic acid and digesting for 72 hours at 4° C. Following partial digestion, the suspension was centrifuged at 12,000 rpm for 20 minutes at 4° C. and the insoluble pellet discarded. The supernatant was dialyzed against several changes of 0.01 M acetic acid at 4° C. (MWCO 3500). The solution was sterilized by adding chloroform (5 ml chloroform to each 900 ml 0.01 M acetic acid) to the LBM hydrolysate. Dialysis of the LBM tissue was continued with two additional changes of sterile 0.01 M acetic acid to eliminate the chloroform. The contents of the dialysis bag were then transferred aseptically to a sterile container. The resultant fluidized composition was stored at 4° C.

EXAMPLE 3

Preparation of Liver Basement Membrane Gel Compositions

To prepare the gel form of LBM, 8 mls of the fluidized form of LBM, as described in Example 2, was mixed with 1.2 ml 10× PBS buffer (10× phosphate buffered saline containing 5 mg/L phenol red); 0.04 N HCl (approx 1.6 ml) was added to adjust the pH to between 6.6 and 7.4 and then 0.05 N NaOH (approx. 1.2 ml) was added to shift the pH to >8.

EXAMPLE 4

Preparation of Liver Basement Membrane Powder

The present invention also contemplates the use of powder forms of liver basement membrane. A powder form of liver basement membrane was prepared by pulverizing liver basement membrane under liquid nitrogen to produce particles ranging in size from 0.1 to 1 mm². The particulate composition was then lyophilized overnight and sterilized to form a solid substantially anhydrous particulate composite. Alternatively, a powder form of liver basement membrane can be formed from fluidized liver basement membranes by drying the suspensions or solutions of comminuted liver basement membrane.

EXAMPLE 5

Preparation of Extracts of Liver Basement Membrane

Extraction buffers used for these studies include 4 M guanidine and 2 M urea each prepared in 50 mM Tris-HCl, pH 7.4. The powder form of liver basement membrane (LBM) was suspended in the relevant extraction buffer (25% w/v) containing phenylmethyl sulphonyl fluoride, N-ethyhnaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately or lyophilized for long term storage.

EXAMPLE 6

Surgical Repair of Vocal Cords

Seven healthy adult female mongrel dogs are subjected to bilateral resection of the vocal folds. One side is repaired with a single thickness sheet of LBM, prepared as described herein, which is a resorbable naturally-occurring scaffold. The contralateral side in each dog is left unfilled as a control. The dogs are evaluated at time points ranging from three weeks to several months.

At three weeks, there will be significant remodeling along the framework of the resorbable scaffolds, and there will be deposition of new extracellular matrix, an abundant vascular component, and a dense infiltration of mononuclear cells within the space occupied by the original tissue. The contralateral (control) side will show scar tissue formation partially filling the defect.

EXAMPLE 7

Mechanical Properties of Purified Liver Basement Membrane

Porosity Index. Porosity of a graft material is typically measured in terms of ml of water passed per $cm^2$ $min^{-1}$ at a pressure of 120 mm Hg. The average porosity index of native LBM, purified as described above, was 1.7±1.2 (N=The average porosity indices for peracetic acid-treated LBM and peracetic acid and gamma-irradiated LBM, both purified as described above, were 4.3±2.1 (N=7) and 2.6±1.4 (N=7), respectively.

Suture Retention Strength. The suture retention strength test measures the force required to pull a suture through the material tested. The suture retention strength of native LBM (N=24), purified as described above, was approximately 0.45±0.14 Newtons (0.10±0.03 lbs.).

Ball Burst Testing. The ball burst test measures the force that a material can withstand. The ball burst strength of native LBM (N=3), purified as described above, was 19.66±4.27 Newtons (4.42±0.96 lbs.).

Thickness. The thickness of LBM (N=3), purified as described above, was 0.18±0.02 mm (0.0071±0.0008 inch).

EXAMPLE 8

DNA Content of Purified Liver Basement Membrane

The following table shows DNA assay data for the LBM purfication method described in the present application.
DNA Assay results for the purification method described in the present application:

| LBM Treatment | Average | Standard Deviation | Number of Tests |
| --- | --- | --- | --- |
| Native | 0.303 | 0.263 | 3 |
| PAA | 0.429 | 0.380 | 3 |
| PAA + gamma | 0.572 | 0.509 | 3 |

DNA Assay results for alternative purification method #1:

| LBM Treatment | Average | Standard Deviation | Number of Tests |
|---|---|---|---|
| Native | 16.15 | 9.71 | 32 |
| PAA | 6.1 | 5.52 | 30 |
| PAA + gamma | N/A | N/A | N/A |

DNA Assay results for alternative purification method #2:

| LBM Treatment | Average | Standard Deviation | Number of Tests |
|---|---|---|---|
| Native | 51.02 | 12.31 | 20 |
| PAA | 24.26 | 18.68 | 32 |
| PAA + gamma | N/A | N/A | N/A |

Native—resulting material from the purification method
PAA—native material disinfected with a 0.1% peracetic acid solution
PAA+gamma—disinfected material terminally sterilized with 1 Mrad of gamma irradiation
Values are in terms of micrograms of DNA/milligram dry weight.

These data show that the purification method described in the present application results in purified LBM preparations substantially devoid of DNA relative to other purification methods.

What is claimed is:

1. A purified liver basement membrane graft composition comprising decellularized basement membrane of warm-blooded vertebrate liver tissue, wherein the DNA content of the liver basement membrane is within a set of values with an average of 0.303 and a standard deviation of 0.263 micrograms of DNA per milligram of dry weight of the basement membrane and wherein the graft composition is remodelable upon implantation.

2. The composition of claim 1 wherein the liver basement membrane is fluidized.

3. The composition of claim 1 wherein the liver basement membrane is in a gel form.

4. The composition of claim 1 wherein the liver basement membrane is dried and is in powder form.

5. The composition of claim 1 wherein the liver basement membrane is substantially free of cells of the warm-blooded vertebrate.

6. A liver tissue derived composition for supporting the growth of a cell population, said composition comprising the liver basement membrane composition of claim 1 wherein the liver basement membrane composition of claim 1 is devoid of source liver tissue endogenous cells; and
added nutrients to support the growth of said cell population in vitro.

7. A liver tissue derived composition for supporting the growth of a cell population, said composition comprising culture-ware coated with a matrix comprising the liver basement membrane composition of claim 1 wherein the liver basement membrane composition of claim 1 is devoid of source liver tissue endogenous cells.

8. A collagenous tissue graft structure comprising decellularized liver basement membrane wherein the DNA content of the liver basement membrane is within a set of values with an average of 0.303 and a standard deviation of 0.263 micrograms of DNA per milligram of dry weight of the basement membrane and wherein the graft composition is remodelable upon implantation.

* * * * *